United States Patent
Lee et al.

[11] Patent Number: 5,469,742
[45] Date of Patent: Nov. 28, 1995

[54] ACOUSTIC TEMPERATURE AND FILM THICKNESS MONITOR AND METHOD

[76] Inventors: Yong J. Lee, 2600 E. Renner Rd., Apt. 285, Richardson, Tex. 75082; Butrus T. Khuri-Yakub, 4151 Donald Dr., Palo Alto, Calif. 94306; Krishna C. Saraswat, 12356 Parker Ranch Rd., Saratoga, Calif. 95070

[21] Appl. No.: 28,331

[22] Filed: Mar. 9, 1993

[51] Int. Cl.⁶ .................................................. G01N 29/18
[52] U.S. Cl. .......................... 73/597; 73/644; 374/119; 374/137; 437/8; 437/9
[58] Field of Search ................... 73/597, 644, 643, 73/DIG. 1; 374/117, 119, 137; 437/8, 9, 225

[56] References Cited

U.S. PATENT DOCUMENTS

| | | | |
|---|---|---|---|
| 3,299,707 | 1/1967 | Noel | 374/119 |
| 4,307,616 | 12/1981 | Vasile | 73/643 |
| 4,332,833 | 6/1982 | Aspnes et al. | 427/8 |
| 4,674,332 | 6/1987 | Pace et al. | 73/597 |
| 4,803,884 | 2/1989 | Kaneta et al. | 73/597 |
| 5,240,552 | 8/1993 | Yu et al. | 437/225 |
| 5,286,313 | 2/1994 | Schultz et al. | 73/597 |

Primary Examiner—Hezron E. Williams
Assistant Examiner—Rose M. Finley
Attorney, Agent, or Firm—Flehr, Hohbach, Test, Albritton & Herbert

[57] ABSTRACT

An acoustic temperature and/or film thickness monitoring system for semiconductor wafers in which the velocity of acoustic waves in the wafer is employed to measure temperature and/or thickness.

17 Claims, 5 Drawing Sheets

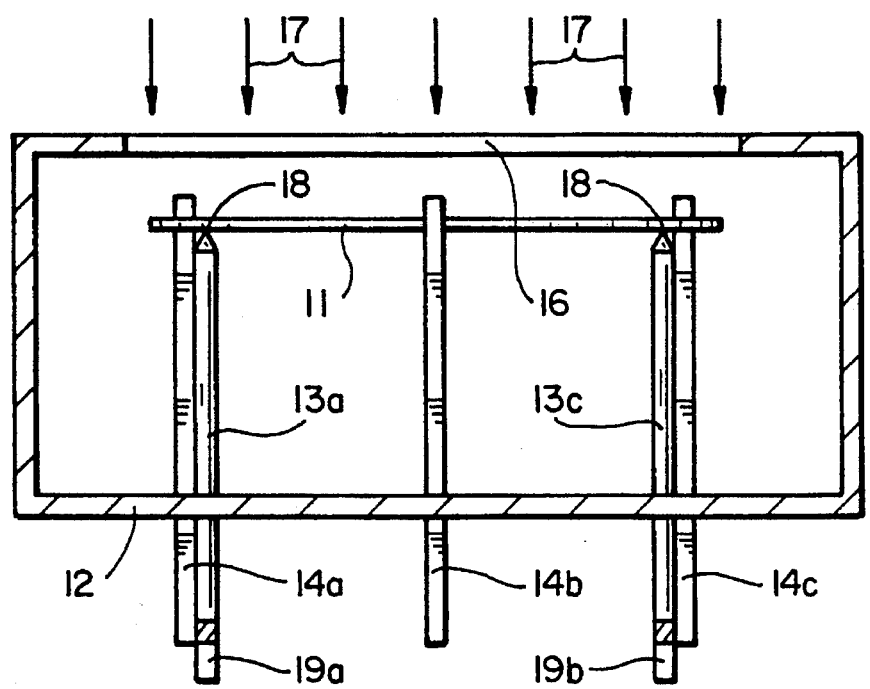
FIG_1
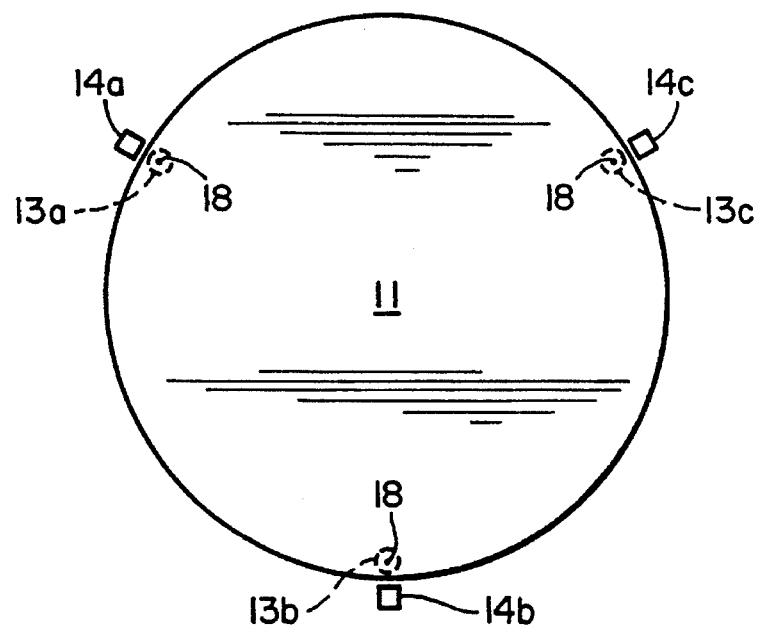
FIG_2

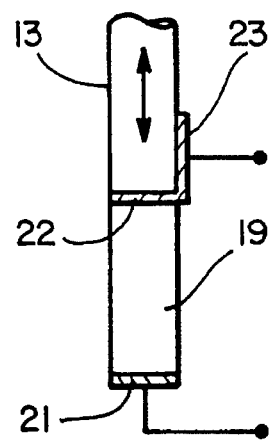
FIG_3
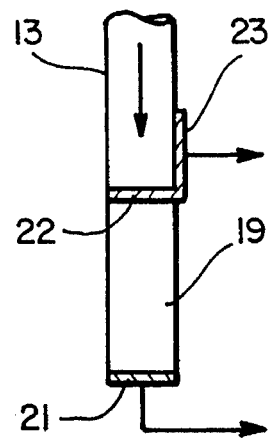
FIG_4
ANTI-SYMMETRIC LAMB WAVE
FIG_5
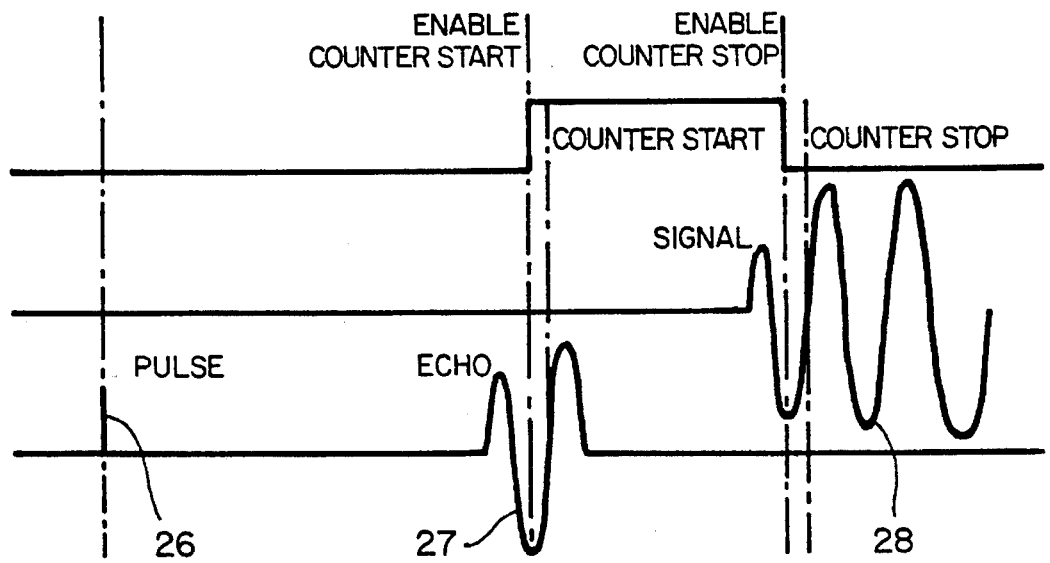
FIG_6

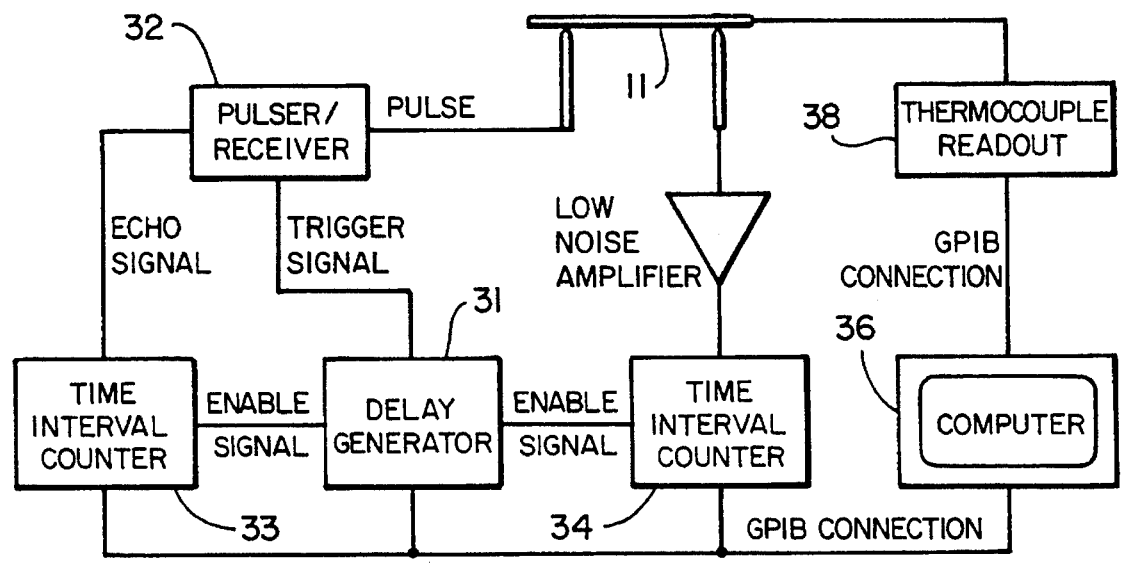
FIG_7
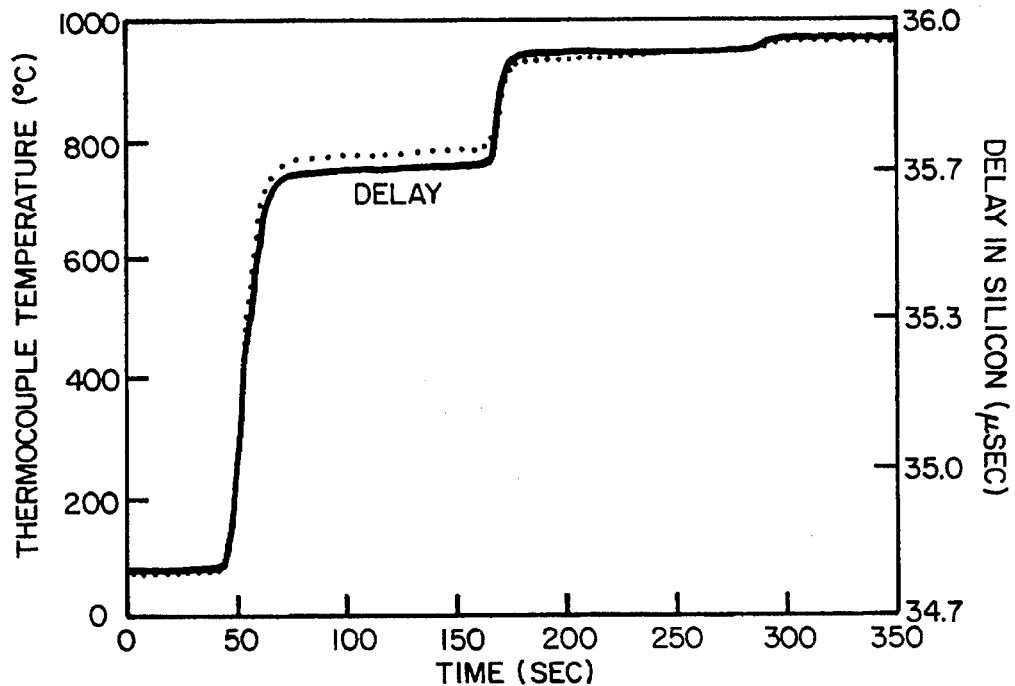
FIG_8

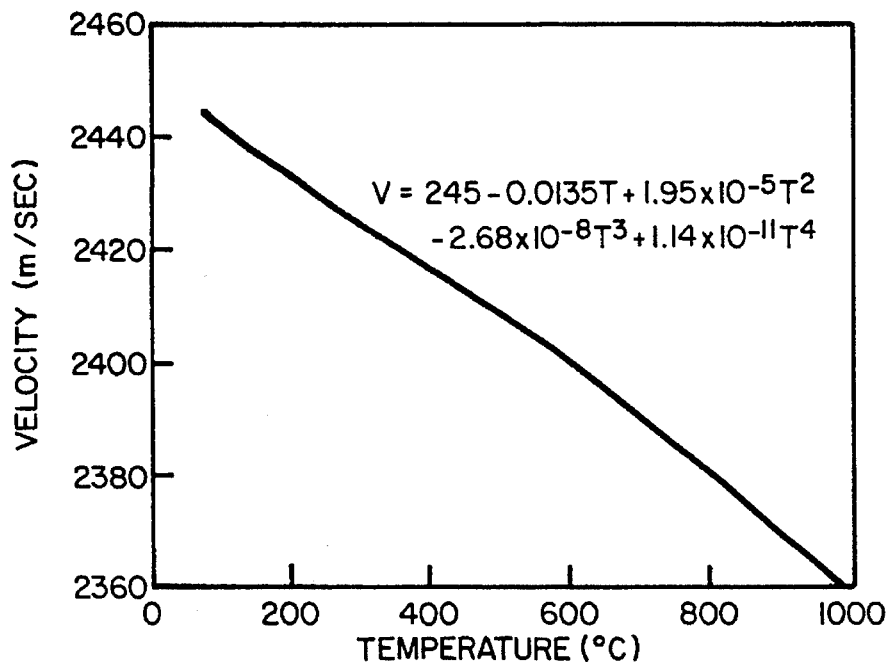
FIG_9
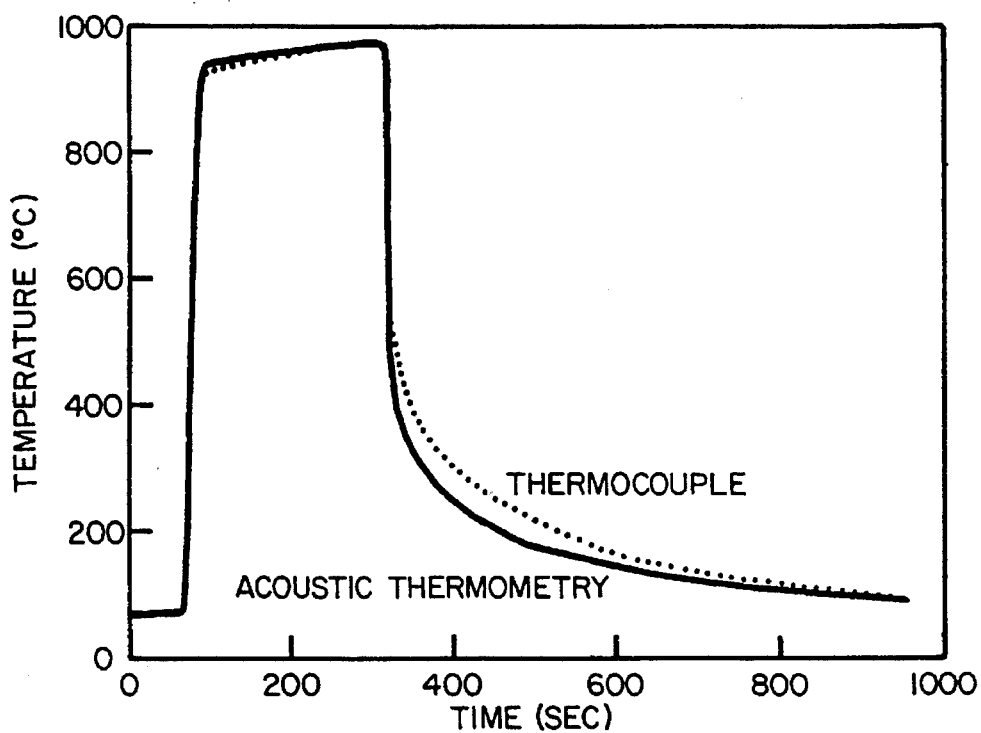
FIG_10

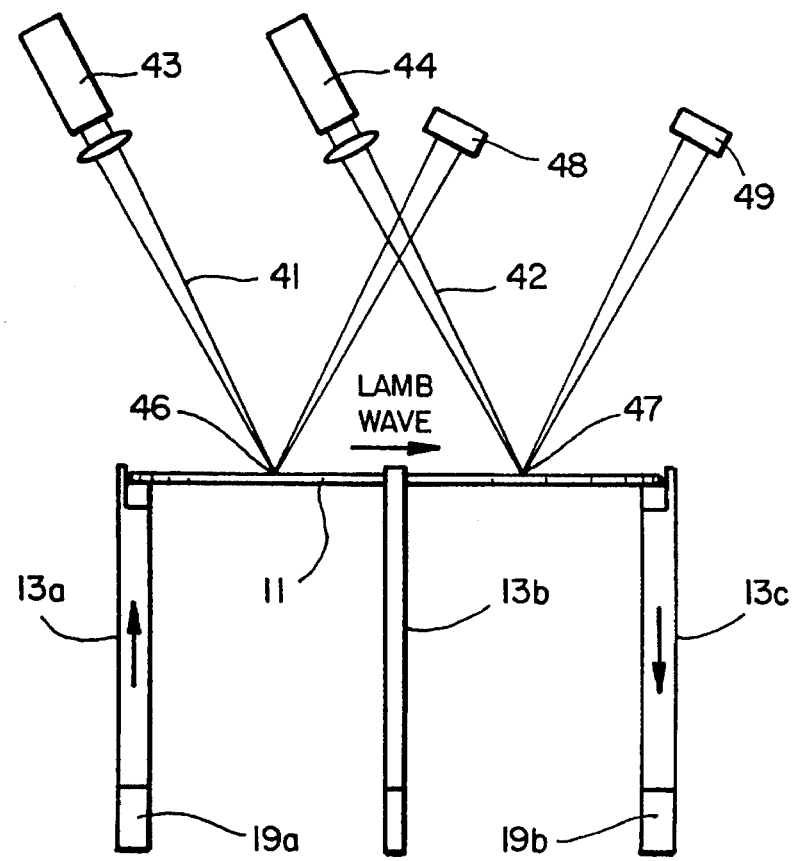
FIG_11
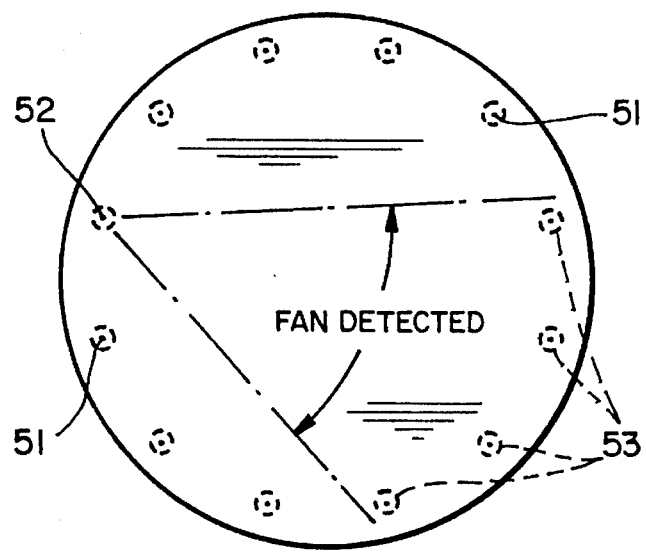
FIG_12

5,469,742

ACOUSTIC TEMPERATURE AND FILM THICKNESS MONITOR AND METHOD

BRIEF DESCRIPTION OF THE INVENTION

This invention relates generally to an acoustic temperature and film thickness monitor and method and more particularly to an acoustic temperature and film thickness monitor and method for measuring the temperature and deposited film thickness of a semiconductor wafer during processing, such as rapid thermal processing, evaporation, ion etching, etc.

BACKGROUND OF THE INVENTION

In rapid thermal processing of semiconductor wafers a wafer is supported in a processing chamber by a plurality of pointed quartz pins, usually three. The low thermal conductivity of the quartz as well as the small contact area at the support point minimizes heat transfer from the wafer into the support rods thereby assuring uniform wafer temperature. The wafer is rapidly heated by thermal radiation from a single or an array of tungsten-halogen lamps which are arranged to provide uniform temperature throughout the wafer.

It is extremely important that the wafer temperature be continually monitored during wafer processing. It is also desirable to monitor the thickness of films which are deposited as the wafer surface during processing. An ideal temperature and thickness sensor has the following characteristics: fast response time to provide accurate and repeatable real time temperature independent of changing wafer conditions, must not disturb the wafer temperature distribution, be insensitive to wafer processing gases and pressures, and inexpensive.

Different temperature dependent physical phenomena have been used to measure the temperature of wafers during processing. One of the most popular temperature sensor, based on lattice vibrations, is the thermocouple. Although the thermocouple is fairly accurate, its must contact the wafer. There are several problems with the contacting technique. First, thermocouples are metallic and serves as heat sinks on the wafer producing temperature non-uniformities. The thermocouple material contacting the wafer contaminates the wafer. Finally, unless the thermocouple is welded or bonded onto the wafer it is difficult to ensure a reliable contact. Thus, thermocouples, although used extensively for calibration purposes are generally not used during actual processing. The most widely used temperature measurement technique in rapid thermal processing is pyrometry. Pyrometry, however, has the significant limitation that its measurements are strongly dependent on the emissivity of the wafer. The emissivity of the wafer is dependent on several factors including film thickness, surface roughness, surface material, and temperature and is difficult predict. Other method of temperature measurement based on emission (black body radiation) are multi-wavelength pyrometry, infrared spectral correlation, and ellipsometry. Another temperature dependent phenomena is thermal expansion. In one such temperature measurement technique, a grating is placed on the wafer and the moiré pattern created by the interference of a laser light grating and an etched grating is studied to measure the local thermal expansion, and thus the temperature. Thermal expansion of the thickness of the wafer and the length of the wafer are also used to measure the temperature. The wide range of temperature measurement schemes reflects the fact that temperature monitoring and control is currently a very important issue in semiconductor processing.

OBJECTS AND SUMMARY OF THE INVENTION

It is an object of this invention to provide an acoustic temperature and film thickness monitor and method for monitoring semiconductor wafer temperature and/or deposited film thickness during processing.

It is another object of the invention to provide an acoustic temperature and/or film thickness monitor and method which employs Lamb waves.

It is another object of the invention to provide an acoustic temperature and/or film thickness monitor in which Lamb waves are excited in the semiconductor wafer through the quartz supports which support the wafer in the processing chamber.

It is another object of the invention to provide an acoustic temperature and/or film thickness monitor which employs Lamb waves excited in the wafer at two different frequencies.

It is another object of the invention to provide an acoustic temperature monitor and method which has a fast response and provides repeatable temperature in real time.

The foregoing and other object of the invention are achieved by exciting acoustic waves in a wafer being processed and measuring the time of flight or velocity of the acoustic waves as they travel through the wafer and converting the time of flight or velocity measurement into temperature and/or film thickness.

A wafer temperature monitor for monitoring the temperature of a wafer as it is being thermally processed including means for generating in said wafer acoustic waves so that the waves propagate through said wafer, means for providing an output signal representative of the time of flight or velocity of said Lamb waves as they propagate through the wafer and means for convening the time of flight or velocity signal to temperature and/or film thickness.

BRIEF DESCRIPTION OF THE DRAWINGS

The foregoing and other objects of the invention will be clearly understood from the following description when read in conjunction with the drawings of which:

FIG. 1 schematically show a wafer supported by quartz rods in the processing chamber of rapid thermal processing equipment;

FIG. 2 is a top plan view of the wafer, wafer guides and wafer supports;

FIG. 3 is an enlarged view of the bottom of a quartz support rod showing an acoustic transducer for exciting extensional acoustic waves in the rod which induce acoustic waves in the wafer;

FIG. 4 is an enlarged view of a quartz support rod showing an acoustic transducer which receives extensional acoustic waves induced in the quartz support rod by acoustic waves in the supported wafer;

FIG. 5 shows an anti-symmetric Lamb wave;

FIG. 6 shows the output of the transducers and the time of flight measurement;

FIG. 7 is a schematic diagram of one embodiment of time of flight measurement electronics;

FIG. 8 shows a calibration measurement of acoustic time delay and temperature as measured by a thermocouple at difference lamp powers;

FIG. 9 shows the measured temperature dependence of Lamb wave velocity;

FIG. 10 shows an actual temperature measurement during rapid thermal processing compared to the temperature taken by a thermocouple;

FIG. 11 shows another time of flight measurement technique; and,

FIG. 12 shows multiple transmitting and receiving rods for obtaining a temperature profile of the wafer by using tomographic techniques.

DESCRIPTION OF A PREFERRED EMBODIMENT

Referring to FIGS. 1 and 2, there is shown a wafer 11 supported in a processing chamber 12 by quartz rods 13 *a–c*. The wafer is held in position by spaced guides 14 *a–c*. The chamber 12 includes a window 16 through which thermal radiation 17 projects. The thermal radiation may for example be supplied by tungsten-halogen lamps. The radiation rapidly heats the wafer as it impinges on the surface of the wafer. The quartz support rods 12 include pointed tips 18 which provide minimal contact area to the wafer, thereby minimizing the contacting effect of the quartz pins.

A PZT longitudinal or shear wave acoustic transducer is bonded at the end of spaced quartz support rods. Referring particularly to FIGS. 1 and 3, the transducers 19 are of predetermined thickness which determines the frequency of acoustic waves and have metalization 21 and 22 for application of electrical voltage thereacross to generate the acoustic waves. Preferably, the lower end of the corresponding quartz rod 12 is metalized on the bottom and along the side edge as shown at 23, whereby electrical connection can be easily made to the spaced metalization 21 and 22. Voltage applied across the metalization causes mechanical displacement which launches longitudinal or shear acoustic waves at a frequency dependent on the transducer thickness along the length of a quartz pin. The longitudinal or shear wave in a quartz pin is coupled into the silicon wafer via the sharp point 18 at the end of the quartz rod. The sharp point localizes the point of excitation allowing for a more controlled coupling of acoustic energy into the wafer. The sharp tip also has the effect of amplifying the displacement caused by the longitudinal or shear wave.

If a low frequency transducer is employed, Lamb waves are excited in the wafer. If a high frequency transducer is employed, longitudinal, or shear waves are propagated through the pin. At high frequency the thickness of the wafer is several wavelengths of the excited waves. Thus surface, longitudinal and shear waves are excited separately. A continuation of these waves at low frequency excite Lamb waves. As a numerical example, at 100 mHz, the wavelengths are 50 microns, 55 microns and 85 microns for the surface, shear and longitudinal waves, respectively. Thus, these waves can be excited separately. All of the acoustic waves have velocities which are dependent on temperature. Only surface and Lamb or plate waves are affected by film thickness. The velocity is measured by measuring the time it takes the particular acoustic wave to travel from the exciting pin to a receiving pin.

Among the various acoustic modes generated in the silicon wafer by the quartz pin is the zero order antisymmetric Lamb wave illustrated in FIG. 5. The Lamb wave propagates along the plane of the silicon wafer, and its velocity dispersion characteristics are a function of wafer bulk temperature. For any frequency of excitation, the velocity of a Lamb wave will vary with temperature, and for any temperature, the velocity of the Lamb wave will vary with the frequency of the transmitted wave. The Lamb wave travels across the wafer from one quartz rod to a spaced quartz rod. The Lamb wave is coupled to the spaced quartz rod and generates a longitudinal wave in that quartz rod. The resulting displacement at the end of the pin is converted into a voltage by the associated transducer 19. The same excitation and detection takes place for the other acoustic waves.

Referring to FIG. 6, a pulse 26 is shown applied to the transmitting transducer, the pulse generates a longitudinal wave of predetermined frequency in the associated quartz rod. As described above the longitudinal wave is coupled to the wafer to generate a Lamb wave in the wafer; however, the wave is also reflected and is therefore detected by the transmitting transducer which provides an echo signal 27. The Lamb wave travels to the spaced rod and generates a longitudinal wave 28 in the other spaced quartz rod. The time of flight of the Lamb wave in the wafer is obtained by subtracting the time it takes the longitudinal wave to travel in the two spaced quartz rods from the total time between the transmit pulse of the first transducer and the output of the second transducer. Assuming the rods are of equal length, this time is equal to the time represented between the transmit pulse and its echo output. Therefore the time of flight is obtained by counting the time between like excursions of the waves 27 and 28, FIG. 6. Zero crossing of the pulse echo signal is used to start a time interval counter and the zero crossing on the time of flight signal is used to stop the counter thereby providing the time interval. In a second method two separate time measurements are made. One for the time between transmit and pulse echo and the other for the time between the pulse and the output signal. The pulse echo time is subtracted from the total time of flight in a computer.

Referring to FIG. 7, the implementation of the latter method is illustrated. The delay generator 31 provides a trigger signal to the pulse receiver 32 which generates pulses to excite the transducer at one of the quartz rods. At the same time it enables the time interval counter 33. The echo signal stops the time interval counter 33 which provides the time interval between time of initiation of the pulse and reception of the echo signal. The delay generator 31 also activates the time interval counter 34 which is turned off when a signal is received from the transducer 19 associated with the rod 12. These outputs are applied to a computer which subtracts the two signals. The computer 36 is also connected to a thermocouple readout 38 which can be used to calibrate the monitor.

Referring the FIG. 8, a wafer is irradiated at different lamp powers to elevate its temperature to different levels. The time delay obtained by the time interval counter is then calibrated, whereby, during processing, the delay in microseconds provides the reading of temperature. The computer is provided with either a look-up table which correlates delay to temperature, or a polynomial, such as in FIG. 9, which relates velocity to temperature. Each of these can be obtained from a calibration run and used to convert time of flight into temperature.

In one example, the monitor was tested and the results shown in FIG. 10 were obtained. This shows a good correlation between acoustic thermometry and thermocouple measurements.

Referring to FIG. 11, the Lamb wave delay or velocity can be obtained by the use of beams 41, 42 from laser 43, 44 such as helium-neon lasers. The beams 41, 42, focused at two locations 46, 47 at the surface of the wafer. The angular reflection of helium-neon beam is modulated by the Lamb waves in the wafer. The position of the reflected beam is measured by bi-cell detectors 48, 49. The bi-cell detectors provide output signals as the Lamb wave passes locations 46, 47. The signals can be processed electronically to obtain the time delay which can then be used to convert the time of flight to a temperature by a look of table or a polynomial.

A CW sinusoidal wave may be generated by the transmit transducer. By keeping the propagation characteristics and the quartz rods constant and measuring the phase and amplitude difference between the input to the transmit transducer and the output of the receiver transducer the phase changes in the Lamb waves propagating in the wafer can be measured. The phase change can be used to derive the velocity of the Lamb wave and in turn temperature or film thickness measurements. Because the phase detection scheme relies on measuring the differences in phase and amplitude rather than measuring the absolute value, the initial temperature or film thickness needs to be known.

A combination of the two techniques can be used. The pulse echo technique can be used to measure the initial temperature or film thickness prior to processing. During processing when detection time becomes crucial the phase and amplitude technique can be used.

The surface wave in particular can be used to measure temperature and film thickness in the same fashion as we used the Lamb waves. The dependence of the surface wave velocity on temperature and film thickness is different from that of the Lamb waves; however, these functions can be evaluated and used to find temperature and thickness.

The quartz pins can be spring loaded and made to clamp the wafer against stops protruding in from above the edges of the wafer. With spring loading, reliable Hertzian contacts between the quartz tips and the wafer can be made at more than three points. FIG. 12 shows a plurality of contact points 51 on the periphery of the wafer. With a large number of quartz pins located at the perimeter of the wafer, temperature mapping of the wafer will be possible using tomography techniques. One transmit pin 52 will launch Lamb waves which fan out from the point 52 and are received by a plurality of receive pins 53 located near the edges of the wafer. Because the Lamb waves will travel different areas of the wafer which will be at different temperatures, the velocity of the Lamb waves (adjusting for anisotropy) will vary. By transmitting the acoustic wave which fans out from sequential transducer pins, and by receiving the fan beam, a plurality of velocity measurements are obtained. This information can be processed by a computer to provide a tomographic temperature map of the wafer.

In many applications, it is not only important to monitor the temperature of the wafer, but it may also be important to monitor the thickness of films which are being grown on the surface of the wafer. The velocity of the Lamb waves in the wafer depends on temperature, frequency and thickness: V=F[temperature(T), thickness(h) & frequency(f)]. Thus, transducers attached to different pins are selected of different thicknesses to operate at different frequencies. With two measurements of velocity $V_1$ and $V_2$, we have two equations: $V_1= F(T, h, f_1)$ and $V_2=F(T, h, f_2)$. Since $f_1$ and $f_2$ are known, the equations can be solved for temperature (T) and thickness (h). Using the tomographic technique described above with two frequencies, the temperature and surface profile of the wafer can be obtained.

The pin—pin method of coupling and receiving ultrasonic waves can be used for material characterization. For instance, one pin could send and the other receive signals due to plate modes in a wafer and the velocity of the acoustic wave is measured. Longitudinal and shear waves in the bulk can also be used to determine material constants in a sample. Contact between the pins and samples could be removed, the same rotated, and then contact reestablished and a new measurement of the speed of the acoustic wave made. This process is repeated to acquire a measure of the wave velocity as a function of angle. Thus, the anisotropy is measured. This measurement could be used with other modes of propagation to measure surface wave and bulk wave properties of samples. In this fashion, this technique competes well (no water necessary) with acoustic microscope measurements of material properties.

As described above, a cone point contact is used to launch the acoustic waves in the material. A wedge can be used as a line source of acoustic waves instead of a point source. The waves from such a source would be more directional than the fan shape from a point.

Thus, there has been described a novel method of measuring parameters of wafers, such as temperature and thickness during processing and for providing profiles of such parameters.

What is claimed is:

1. The method of measuring a characteristic of a semiconductor wafer during processing which comprises the steps of launching an acoustic wave in the wafer at one location so that the acoustic wave propagates through the wafer, measuring the elapsed time required for the acoustic wave to travel between two spaced locations on the wafer, and converting said elapsed time to a measure of said characteristic between said two locations;

wherein the elapsed time is measured between a number of spaced locations and wherein said elapsed times are converted into a profile of the characteristic of said wafer.

2. The method of claim 1 wherein the characteristic is temperature.

3. The method of claim 1 wherein the characteristic is thickness.

4. The method of measuring a characteristic of a semiconductor wafer while the wafer is being processed in a processing chamber, comprising supporting the wafer in the processing chamber on one end of spaced support rods, launching an incident longitudinal or shear acoustic wave at the other end of a first of said support rods whereby said incident acoustic wave induces a travelling acoustic wave in the wafer at said one end, said travelling acoustic wave propagating through the wafer, measuring the velocity of said travelling acoustic wave between two spaced locations in said wafer, and converting said velocity to an indication of said characteristic between said two spaced locations.

5. The method as in claim 4 wherein the acoustic wave is a Lamb wave and the velocity is measured by reflecting laser beams from said two spaced locations and detecting deflection of said beams due to passage of said Lamb wave past said two spaced locations.

6. The method as in claim 5 wherein said Lamb wave induces a longitudinal or shear wave in a second of said spaced support rods and in which the velocity of the Lamb wave is measured by measuring the time lapse between the launching of said longitudinal or shear wave at one end of said first support rod and the time the induced longitudinal or shear wave is received at the other end of said second support rod and subtracting the time of travel of the longitudinal or shear acoustic waves in said rods.

7. The method of measuring one of temperature, thickness, or temperature and thickness of a semiconductor wafer while the wafer is being processed in a processing chamber, comprising supporting the water in the processing chamber on one end of spaced support rods, launching incident longitudinal or shear acoustic waves at the other end of at least two of said support rods, at different frequencies, whereby said incident acoustic waves induce travelling acoustic waves of different frequencies in the wafer at said one end of said rods, said travelling acoustic waves propagating through the wafer, measuring the velocity of said travelling acoustic waves of said different frequencies between two spaced locations in said wafer, and converting said velocities to an indication of one of temperature, thickness, or temperature and thickness of the wafer between said two spaced locations.

8. The method of claims 4 or 7 wherein said one end of the support rods is shaped to minimize a contacting effect of said rods with said wafer.

9. The method of claim 8 wherein said contacting effect is said support rods sinking heat from the wafer during said processing.

10. The method of claims 4 or 7 wherein said one end of the support rods is shaped to localize a point of excitation of said travelling acoustic wave in said wafer and amplify a displacement in said wafer caused by said incident longitudinal or shear wave.

11. The method of claims 4 or 7 wherein said one end of the support rods is shaped to minimize a contacting effect of said rods with said wafer, localize a point of excitation of said travelling acoustic wave in said wafer, and amplify a displacement in said wafer caused by said incident longitudinal or shear wave.

12. The method of claim 10 wherein said shaped one end of the support rods is a sharp point.

13. The method of claim 10 wherein the support rods are made of quartz.

14. The method of measuring a characteristic of a semiconductor wafer while the wafer is being processed in a processing chamber, comprising supporting the wafer in the processing chamber on one end of spaced support rods, launching an incident longitudinal or shear acoustic wave at the other end of at least one of said support rods whereby said incident acoustic wave induces a Lamb wave in the wafer at said one end, said Lamb wave propagating as a fan beam through the wafer, measuring the velocity of said Lamb wave in a plurality of directions along said fan beam between two spaced locations in each of said directions in said wafer, repeating velocity measurements in a plurality of directions along the fan beam for fan beams launched from different radial positions, and processing said velocities to provide a tomographic image of said characteristic.

15. A system for monitoring a characteristic of a semiconductor wafer during processing, comprising a plurality of spaced support rods for supporting the wafer from one end, a longitudinal or shear wave transducer mounted on the other end of at least one support rod for inducing incident longitudinal or shear acoustic waves of predetermined frequency in said rod, whereby said incident acoustic waves launch travelling acoustic waves in the wafer, means for measuring the velocity of said travelling acoustic waves between two spaced locations, and means for converting said velocity to an indication of said characteristic of the wafer between said two spaced locations.

16. A system as in claim 15 wherein a second transducer is mounted on the other end of another of said spaced support rods whereby said second transducer detects transmitted longitudinal or shear acoustic waves induced in said another of said spaced support rods by the travelling acoustic waves in said wafer, and said means for measuring the velocity measures the elapsed time between launching of said incident acoustic waves by said longitudinal and shear wave transducer, and reception of said transmitted waves by said second transducer and subtracting the time of travel of said incident and transmitted longitudinal or shear waves in said support rods.

17. A system as in claim 15 wherein first and second lasers project beams at said spaced locations on said wafer and first and second detectors detect the reflected beams and provide an output signal when the travelling acoustic wave travels past said Spaced locations and deflects the reflected beams, thereby providing an indication of velocity of the travelling acoustic wave between said two locations.

\* \* \* \* \*